(12) United States Patent
Bhandar et al.

(10) Patent No.: US 11,724,026 B2
(45) Date of Patent: Aug. 15, 2023

(54) INFUSION PUMP WITH TUBE LOADING GUIDANCE AND CONFIRMATION

(71) Applicants: BAXTER INTERNATIONAL INC., Deerfield, IL (US); BAXTER HEALTHCARE SA, Glattpark (CH)

(72) Inventors: Bhagyesh Kishore Bhandar, Grayslake, IL (US); Steven Ward Fischer, Gurnee, IL (US); Aaron M. Hexamer, Grayslake, IL (US); Jiri Slaby, Buffalo Grove, IL (US); Jason Andrew Maine, Hamlin, NY (US); Scott Christian Ofslager, Albion, NY (US); Morris Wilson Wallace, Spring Grove, IL (US); Keerthika Lakshmi Niharika Chinthapalli, Round Lake, IL (US); Peter M. Bojan, Grayslake, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 5 days.

(21) Appl. No.: 16/413,037

(22) Filed: May 15, 2019

(65) Prior Publication Data
US 2019/0351138 A1 Nov. 21, 2019

Related U.S. Application Data

(60) Provisional application No. 62/671,858, filed on May 15, 2018.

(51) Int. Cl.
*A61M 5/168* (2006.01)
*A61M 5/50* (2006.01)
*A61M 39/28* (2006.01)

(52) U.S. Cl.
CPC .... *A61M 5/16813* (2013.01); *A61M 5/16831* (2013.01); *A61M 5/16859* (2013.01);
(Continued)

(58) Field of Classification Search
CPC .......... A61M 5/16813; A61M 5/16831; A61M 5/16859; A61M 2005/16863;
(Continued)

(56) References Cited

U.S. PATENT DOCUMENTS 5,312,334 A * 5/1994 Hara ..................... A61M 5/142
128/DIG. 13
5,437,635 A * 8/1995 Fields ............... A61M 5/16813
604/153
(Continued)

FOREIGN PATENT DOCUMENTS

EP 1529546 A1 5/2005
GB 2312055 A * 10/1997 ............ A61M 5/172
(Continued)

OTHER PUBLICATIONS

International Search Report and Written Opinion dated Aug. 20, 2019 in corresponding PCT Application No. PCT/US2019/032442 (15 Pages).
(Continued)

*Primary Examiner* — Tiffany Legette
(74) *Attorney, Agent, or Firm* — K&L Gates LLP

(57) ABSTRACT

An infusion pump includes a housing with a door pivotally mounted to the housing, a tube channel on the housing configured to hold a tube in the infusion pump, a pumping mechanism including a shuttle, and a slide clamp ejection device.

13 Claims, 13 Drawing Sheets

(52) U.S. Cl.
CPC .......... *A61M 5/5086* (2013.01); *A61M 39/28* (2013.01); *A61M 2005/16863* (2013.01); *A61M 2205/3313* (2013.01); *A61M 2205/3317* (2013.01); *A61M 2205/3368* (2013.01); *A61M 2205/3375* (2013.01); *A61M 2205/505* (2013.01); *A61M 2205/587* (2013.01); *A61M 2205/6081* (2013.01)

(58) Field of Classification Search
CPC ........ A61M 2205/12; A61M 2205/121; A61M 2205/128; A61M 5/14228; A61M 5/16881; A61M 2205/14; A61M 2205/3313; A61M 2205/3317; A61M 39/28

See application file for complete search history.

(56) References Cited

U.S. PATENT DOCUMENTS

| | | | | |
|---|---|---|---|---|
| 5,782,805 | A * | 7/1998 | Meinzer | G16H 20/17 604/67 |
| 8,628,311 | B2 * | 1/2014 | Oskin | A61M 2205/12 606/27 |
| 2010/0106082 | A1 * | 4/2010 | Zhou | A61M 5/14232 604/67 |
| 2011/0010595 | A1 | 1/2011 | Whetsel | |
| 2013/0238261 | A1 * | 9/2013 | Denis et al. | A61M 2205/12 604/151 |
| 2013/0031783 | A1 | 11/2013 | Ballantyne et al. | |
| 2013/0317837 | A1 * | 11/2013 | Ballantyne | A61M 1/34 705/2 |
| 2014/0010052 | A1 | 1/2014 | Ueda et al. | |
| 2014/0100526 | A1 * | 4/2014 | Ueda et al. | A61M 5/16813 604/151 |
| 2014/0018807 | A1 | 7/2014 | Kamen et al. | |
| 2014/0188076 | A1 * | 7/2014 | Kamen et al. | A61M 5/172 604/506 |
| 2016/0101227 | A1 * | 4/2016 | Norris et al. | A61M 2205/12 604/29 |
| 2017/0342973 | A1 * | 11/2017 | Ikeda et al. | A61M 5/16813 |
| 2018/0221643 | A1 * | 8/2018 | Hetchler | A61M 39/281 |

FOREIGN PATENT DOCUMENTS

| | | |
|---|---|---|
| JP | H1265973 A | 10/1989 |
| JP | H0615001 A | 1/1994 |
| JP | H11507860 A | 7/1999 |
| JP | 2007222485 A | 9/2007 |
| JP | 2007528236 A | 10/2007 |
| JP | 2008289635 A | 12/2008 |
| WO | WO 2017/023489 A1 | 2/2017 |
| WO | WO 2017023489 A1 * | 2/2017 ........ A61M 5/16877 |
| WO | 2017204092 A1 | 11/2017 |

OTHER PUBLICATIONS

Written Opinion for Application No. 11202011036V dated Jul. 25, 2022.

Notice of Reasons for Refusal for Japanese Patent Application No. 2020-558869 dated Mar. 20, 2023.

* cited by examiner

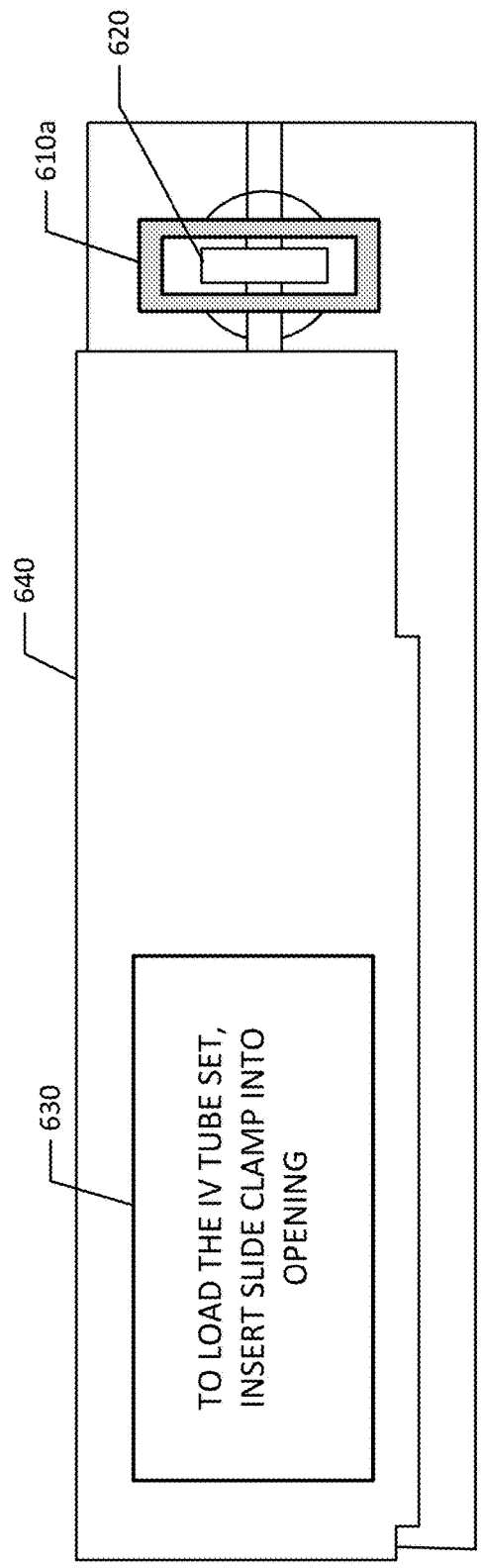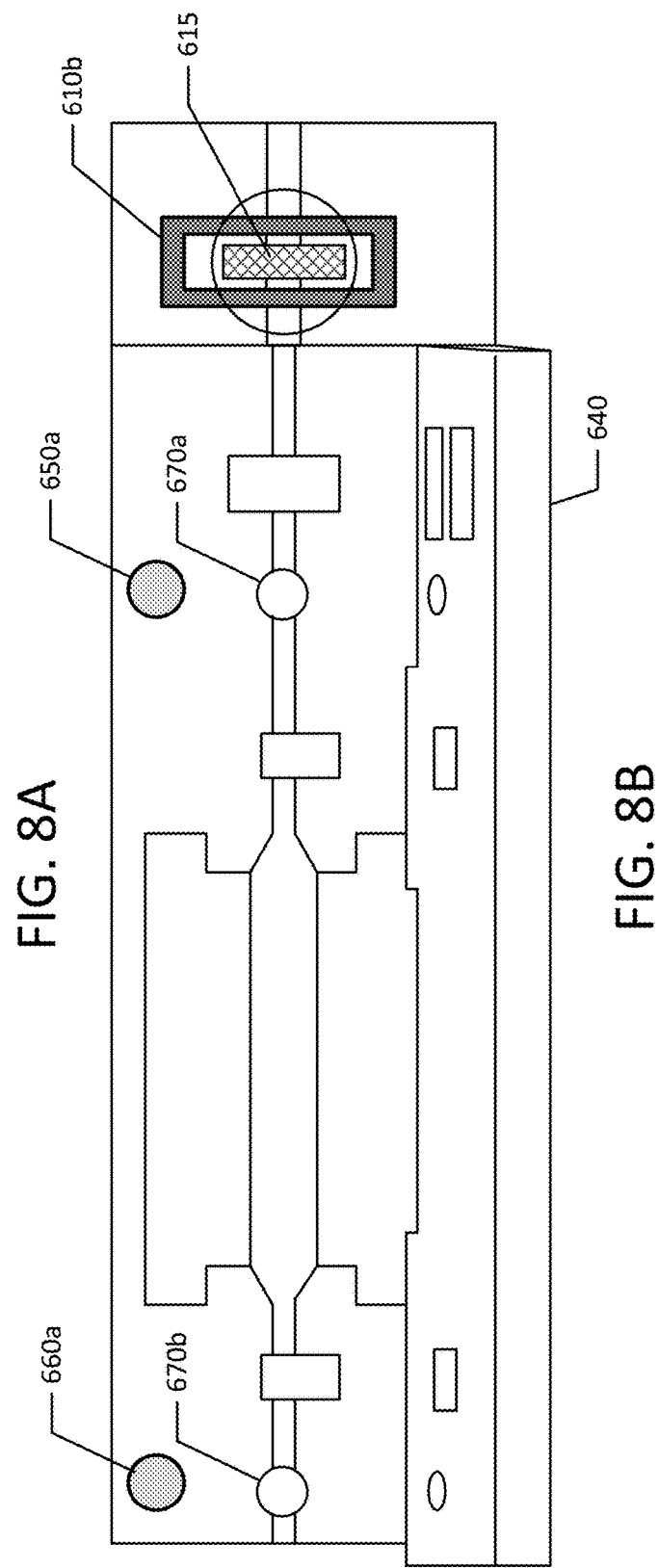
FIG. 8A
FIG. 8B

INFUSION PUMP WITH TUBE LOADING GUIDANCE AND CONFIRMATION

RELATED APPLICATIONS

This application claims the benefit of and priority to U.S. Provisional Patent Application No. 62/671,858 filed May 15, 2018, entitled "INFUSION PUMP," which is incorporated herein by reference in its entirety.

BACKGROUND

Previous medical infusion pumps have comprehended a wide variety of methods for pumping fluids into a patient. The most common of these methods has been a peristaltic pump. In a peristaltic pump, a plurality of actuators or fingers serve to massage a parenteral fluid delivery tube in a substantially linear progression. The primary problem associated with peristaltic pumping technology is that the tube is repeatedly deformed in an identical manner, thereby over the course of time destroying the elastic recovery properties of the tube so that the tube maintains a compressed aspect. This destruction of the elastic recovery properties of the tube results in the volumetric output of the pump changing markedly over time. Another common type of pump used in the volumetric delivery of medical fluids is commonly known as a cassette pump. Although cassette pumps do not display the fairly rapid degradation of performance as evidenced in a peristaltic pump, they require a fairly elaborate pump cassette to be integrated with the IV tube. This added expense of having to change a cassette along with an IV set every time an operator wishes to change the medicament delivered to the patient, significantly raises the cost of patient care. Additionally, as both peristaltic and cassette pumps, as well as other infusion devices present in the market, require a fairly elaborate knowledge of the specific pumping device to ensure that the IV set is loaded appropriately, generally medical infusion pumps were purely the purview of the nursing or medical staff in a hospital environment.

The necessity of manually loading a set into an IV pump is universal in the art. Generally, when a standard IV set is used, in addition to the rapid degradation of accuracy mentioned above, difficulty is encountered in correctly loading the set into those pumps presently in the art. The state of the art of loading technology as it relates to medical infusion pumps has progressed only to the state of enclosing the IV tube between a pumping device and a door or cover and adding progressively more elaborate sensors and alarms to assure that the tube is correctly loaded into the pump. Even so, loading errors may occur requiring great efforts on the part of hospital staffs to ensure that critical errors are minimized.

The state of the art in infusion pumps also includes the requirement of manually assuring that a free-flow condition of medicament does not occur when an IV set is installed or removed from a pump. Although hospital staffs exercise great care and diligence in their attempts to assure that free-flow conditions do not occur, a demonstrable need for additional precautions directed to the prevention of a free-flow condition has been a continuous concern of healthcare workers.

SUMMARY

The instant invention provides for an infusion pump wherein the pump has a pumping body, which consists of a v-shaped groove extending longitudinally along a pump assembly and has associated therewith a fixed, and a moveable jaw and a plurality of valves located at either end of the v-shaped groove or shuttle.

In operation, an operator such as a nurse or patient would commence infusion of a medicament by inserting a standard IV set tube into a tube-loading orifice located on the front of the pump. Additionally, the operator would simultaneously insert a slide clamp, which is associated with the tube into an appropriate slide clamp orifice located upstream, i.e. more toward the fluid source, of the tube-loading orifice. The operator would then actuate a tube loading sequence to load the tube into a tubeway. In an example, a series of pawls and a moveable upper jaw would serve to seize the tube and draw it into a tubeway, part of which is comprised of the v-shaped groove and valves. As the loading cycle progresses, the jaws and pawls close about the tube capturing the tube within the tubeway. Sequentially as the valves close to occlude the tube, the slide clamp would be moved to a position such that the slide clamp would no longer occlude the tube. Upon receipt of appropriate signals from associated electronics which would determine the pumping speed, allowable volume of air, temperature and pressure, the pump is actuated wherein fluid is drawn from the fluid source and expelled from the pump in a constant and metered amount.

Should the tube be misloaded into the tubeway or the tube-loading orifice, appropriate sensors would determine the existence of such a state and effect an alarm directed thereto. At the end of the infusion, actuation by an operator would serve to automatically close the slide clamp and release the tube from the pump.

The pump comprehends a variety of sensors directed to improve the safety of the infusion of medicament and which provide information on the state of the fluid passing through the pump. For example, the sensors provide information regarding the state of various mechanical subassemblies within the pump itself such as a positional location of the shuttle or v-shaped slot aforementioned, valve operation, slide clamp location, and misload detection.

The sensors relating to the state of the fluid being passed through the pump have themselves been improved with regard to accuracy. This has been accomplished by the development of a method of making contact between the sensor and the tube such that the contact is normal to the tube and the tube is placed in contact with the various sensors in such a way that there is neither a volumetric nor a stress gradient across the tube.

Aspects of the subject matter described herein may be useful alone or in combination with one or more other aspects described herein. In an exemplary aspect of the present disclosure, an infusion pump includes a housing with a door pivotally mounted to the housing.

In accordance with another exemplary aspect of the present disclosure, which may be used in combination with any one or more of the preceding aspects, the infusion pump includes a tube channel on the housing configured to hold a tube in the infusion pump. The tube channel may be positioned at least partially behind the door.

In accordance with another exemplary aspect of the present disclosure, which may be used in combination with any one or more of the preceding aspects, the infusion pump includes a pumping mechanism including a shuttle. The pumping mechanism may be positioned behind the door.

In accordance with another exemplary aspect of the present disclosure, which may be used in combination with any one or more of the preceding aspects, the infusion pump includes a slide clamp ejection device configured to eject a slide clamp from a channel.

In accordance with another exemplary aspect of the present disclosure, which may be used in combination with any one or more of the preceding aspects, the slide clamp ejection device includes a solenoid configured to automatically eject the slide clamp based on one or more inputs from one or more sensors arranged on the infusion pump.

In accordance with another exemplary aspect of the present disclosure, which may be used in combination with any one or more of the preceding aspects, the one or more sensors include a first Hall effect sensor configured to detect when the door is positioned in the closed state.

In accordance with another exemplary aspect of the present disclosure, which may be used in combination with any one or more of the preceding aspects, the one or more sensors include an IR sensor configured to detect when the door is latched while positioned in the closed state.

In accordance with another exemplary aspect of the present disclosure, which may be used in combination with any one or more of the preceding aspects, the one or more sensors include a pressure sensor configured to detect the presence of the tube at a load point along the tube channel.

In accordance with another exemplary aspect of the present disclosure, which may be used in combination with any one or more of the preceding aspects, the one or more sensors include a second Hall effect sensor configured to detect that a valve is closed to place the tube in an occluded state.

In accordance with another exemplary aspect of the present disclosure, which may be used in combination with any one or more of the preceding aspects, the infusion pump is configured to initiate an infusion after receiving a confirmation that at least one of the slide clamp is in an ejected state and the door is in a closed state.

In accordance with another exemplary aspect of the present disclosure, which may be used in combination with any one or more of the preceding aspects, the tube is in an occluded state after the slide clamp is inserted within the channel.

In accordance with another exemplary aspect of the present disclosure, which may be used in combination with any one or more of the preceding aspects, the infusion pump includes a sensor that detects the presence of the slide clamp within the channel.

In accordance with another exemplary aspect of the present disclosure, which may be used in combination with any one or more of the preceding aspects, the infusion pump further includes a tube loading guidance system, wherein the tube loading guidance system includes one or more visual cues configured to provide guidance to a user during tube loading.

In accordance with another exemplary aspect of the present disclosure, which may be used in combination with any one or more of the preceding aspects, the visual cues include a first light-emitting diode, a second light emitting diode, and a display. The first and second light emitting diodes are configured to indicate whether a tube is properly or improperly loaded at respective load points on the infusion pump.

In accordance with another exemplary aspect of the present disclosure, which may be used in combination with any one or more of the preceding aspects, the infusion pump further includes an occlusion sensor. The occlusion sensor is configured to determine if an infusion line connected to the infusion pump is blocked.

In accordance with another exemplary aspect of the present disclosure, which may be used in combination with any one or more of the preceding aspects, the occlusion sensor determines if an infusion line is blocked by calculating a slope of a force curve, a slope of a pressure curve, a comparison to a baseline force measurement, a comparison to a baseline pressure measurement, or an area under the force curve.

In accordance with another exemplary aspect of the present disclosure, which may be used in combination with any one or more of the preceding aspects, the infusion pump further includes an accelerometer. The accelerometer is configured to detect an occlusion and/or whether the infusion pump experienced an external impact.

In accordance with another exemplary aspect of the present disclosure, which may be used in combination with any one or more of the preceding aspects, the infusion pump is positioned in a rack with at least one other infusion pump or syringe pump.

Aspects of the subject matter described herein may be useful alone or in combination with one or more other aspects described herein. In another exemplary aspect of the present disclosure, a tube loading guidance system for positioning a tube within an infusion pump housing includes a first visual cue, a second visual cue, and a third visual cue. The first visual cue is configured to indicate both proper and improper loading of a slide clamp in the infusion pump. The second visual cue is configured to indicate both proper and improper loading of the tube at a first load point in the infusion pump. Additionally, the third visual cue is configured to indicate both proper and improper loading of the tube at a second load point in the infusion pump.

In accordance with another exemplary aspect of the present disclosure, which may be used in combination with any one or more of the preceding aspects, the second visual cue and the third visual cue include light emitting diodes.

In accordance with another exemplary aspect of the present disclosure, which may be used in combination with any one or more of the preceding aspects, the light emitting diodes indicate proper loading by illuminating in a first color. Additionally, the light emitting diodes indicate improper loading by illuminating in a second color.

In accordance with another exemplary aspect of the present disclosure, which may be used in combination with any one or more of the preceding aspects, the second visual cue is illuminated based on an output from a pressure sensor associated with the first load point.

In accordance with another exemplary aspect of the present disclosure, which may be used in combination with any one or more of the preceding aspects, the third visual cue is illuminated based on an output from a different pressure sensor associated with the second load point.

Aspects of the subject matter described herein may be useful alone or in combination with one or more other aspects described herein. In another exemplary aspect of the present disclosure, a method of detecting an occlusion includes monitoring a pressure measurement, comparing the pressure measurement to a threshold, and determining an occlusion exists within a tube of an infusion pump when the pressure measurement is greater than the threshold. The pressure measurement may be based on a current ADC, a baseline ADC, and a slope of an ADC-pressure plot. Additionally, the threshold may be based on a selected occlusion detection mode.

In accordance with another exemplary aspect of the present disclosure, which may be used in combination with any one or more of the preceding aspects, the selected occlusion detection mode includes one of a rapid occlusion detection mode and a non-rapid occlusion detection mode.

In accordance with another exemplary aspect of the present disclosure, which may be used in combination with any one or more of the preceding aspects, the threshold is lower for the rapid occlusion detection mode than the non-rapid occlusion detection mode.

To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

Therefore, it is a primary object of the invention to provide for an infusion pump capable of delivering an accurate volume of medicament using a standard infusion set.

It is another object of the invention to provide an infusion pump capable of detecting proper IV tube loading.

It is another object of the invention to provide an infusion pump capable of providing IV tube loading guidance to a user.

It is a further object of the invention to provide automatically actuated slide clamp ejection based on various pump sensor input.

It is another object of the invention to provide occlusion detection for an infusion pump.

It is an additional object of the invention to provide drop detection for an infusion pump.

It is a further object of the invention to provide power management for an infusion pump loaded in a rack configuration.

Additional features and advantages of the disclosed infusion pump are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

FIGS. 8A and 8B are partial views of an infusion pump with tube loading visual indicators, according to an example embodiment of the present invention.

DETAILED DESCRIPTION OF EXAMPLE EMBODIMENTS

Figure 1A:
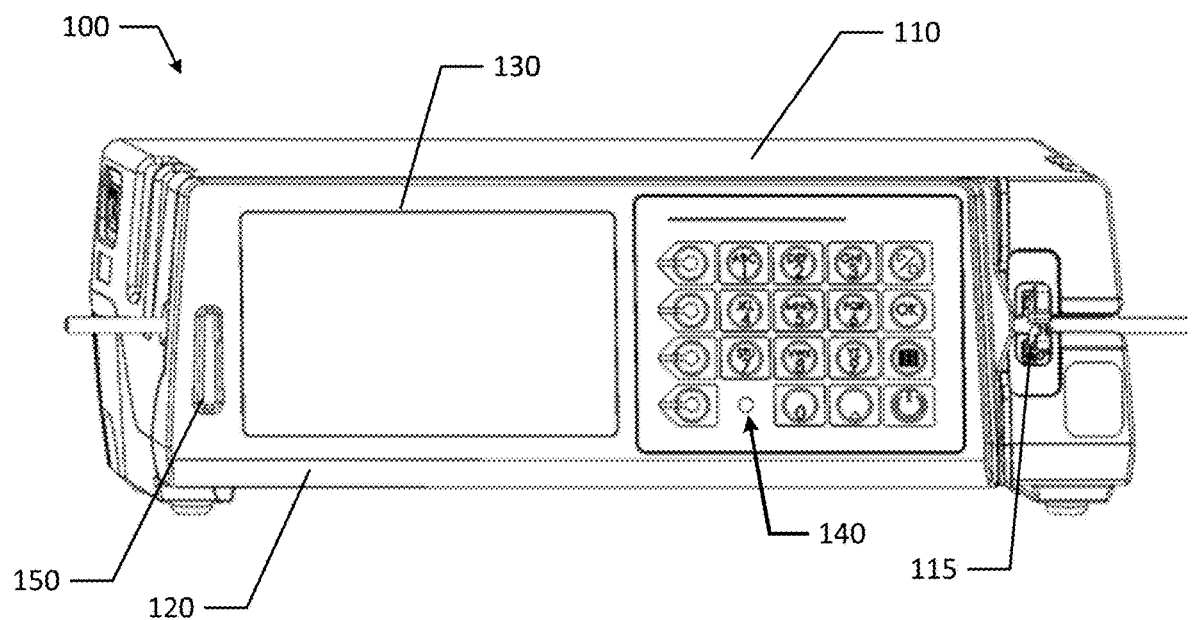
FIGS. 1A and 1B are perspective views of an infusion pump with the door closed according to an example embodiment of the present disclosure.
Figure 1B:
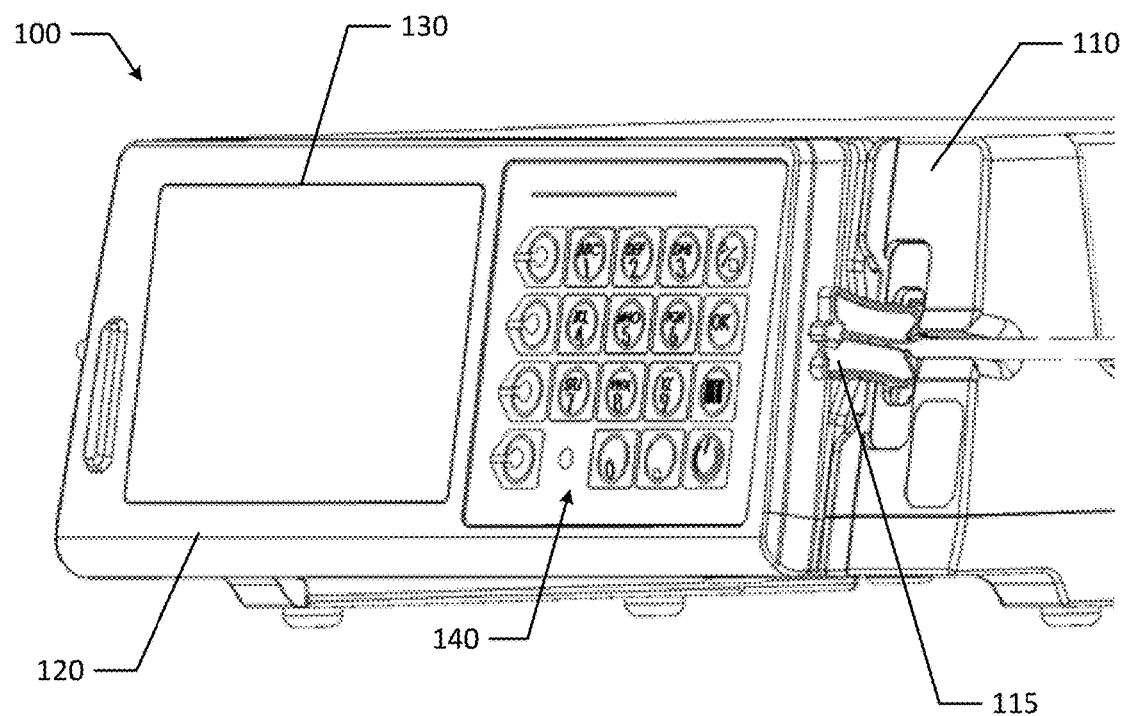

The below disclosure relates to an infusion pump 100. Infusion pump 100 may employ a pump assembly and other features such as and not limited to those described in U.S. Pat. No. 6,213,738; a volumetric infusion pump with automatic tube load described in U.S. Pat. No. 6,123,524; a volumetric infusion pump described in U.S. Pat. No. 6,013,057; a volumetric infusion pump described in U.S. Pat. No. 6,129,517; a volumetric infusion pump described in U.S. Pat. No. 6,195,887; a volumetric infusion pump described in U.S. Pat. No. 6,213,723; and a peristaltic pump described in GB Application No. 2238083A, the entirety of which are incorporated herein by reference. The above examples are non-limiting and the concepts disclosed herein could apply to other medical devices and/or infusion pumps such as a syringe pump.

Referring to FIGS. 1A, 1B, 1C and 1D, an infusion delivery system, such as an infusion pump 100 is used to deliver fluids (e.g., medications or nutrients) to a patient in predetermined quantities. The infusion pump 100 includes a housing 110, a door 120 pivotally connected to the housing 110, a display 130, and a keypad 140. The display 130 and keypad 140 are located on the door 120 along with beacon 150. The display 130 and the keypad 140 are used to program the infusion pump 100, and more specifically, a processor in the pump to set the fluid delivery amount, etc., which is later communicated to the pumping mechanism. It should be appreciated that in various other embodiments, one or more elements of the display 130 and the keypad 140 could be combined in central touch screen.

Beacon 150 may be used as an indicator beacon that emits light or sound to indicate operational states or status of pump 100. For example, when the pump 100 is operating normally and infusing fluids, the beacon 150 may emit a solid green light. During a medium priority alarm, the beacon 150 may emit a flashing yellow light. Similarly, during a high priority alarm, the beacon may emit a flashing red light. The beacon 150 may emit other combinations of colors at various intervals (e.g., pulsing, blinking, solid light) or other audible alerts to indicate the operational state or status of pump 100.

When the pump 100 is in use, fluids may move through a tube loaded into the pump 100. The tube 160 is loaded along the tube channel 162 on the pump 100. Along the tube channel 162, the tube passes through a slide clamp 115, an ultrasonic air sensor 172, an upstream pressure sensor 174a, an upstream valve 176a, the shuttle pumping region 180, a downstream valve 176b, and a downstream pressure sensor 174b. Positioned on the door 120 are other tube engagement features, such as indentions 186a, 186b and tube guide 190.

The tube guide 190 is adapted to maintain the tube's position in the shuttle pumping region 180.

Figure 1C:
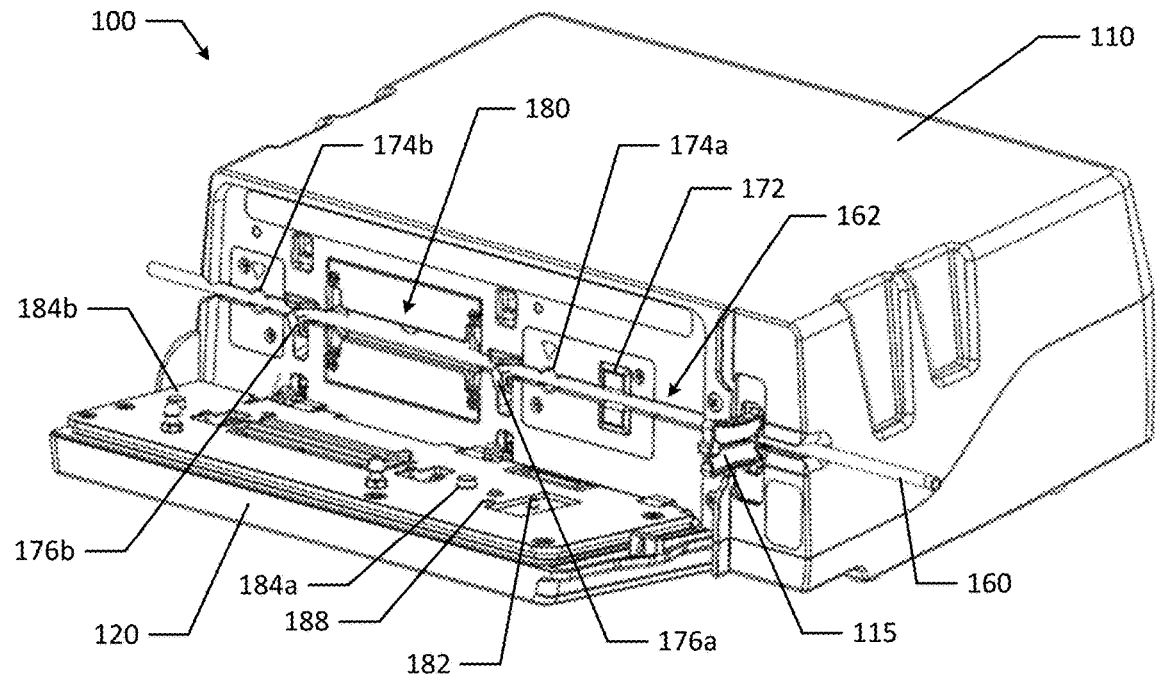
FIGS. 1C and 1D are perspective views of an infusion pump with the door open according to an example embodiment of the present disclosure.
Figure 1D:
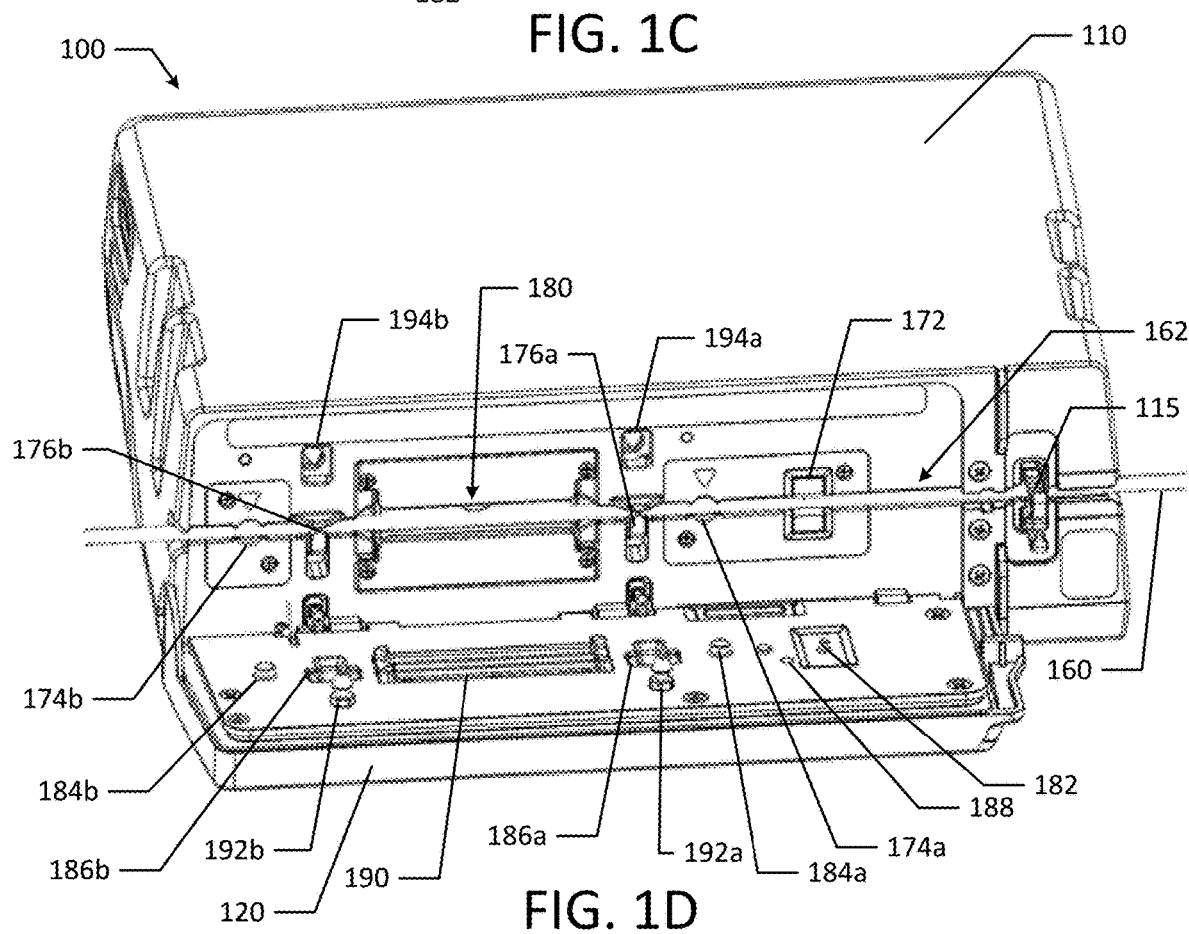

As illustrated in FIGS. 1C and 1D, the pressure sensors 174a, 174b have corresponding door structures (e.g., protrusions or setscrews) that ensure the tube 160 is sufficiently held against the respective sensor. For example, protrusions 184a and 184b correspond to pressure sensors 174a, 174b. Additionally, protrusion 182 corresponds to ultrasonic air sensor 172. There may also be corresponding door indentions for each of the valves 176a, 176b. For example, indentions 186a and 186b (e.g., t-shaped indentions illustrated in FIG. 1D) are configured to prevent the tube from dislodging or "snaking" outside of the tube channel. As illustrated, the indentions 186a, 186b in door 120 are sized and shaped to prevent the tube 160 from "walking" out of valves 176a, 176b.

The door 120 may also include pegs or door latches 192a and 192b that correspond to door mounting apertures 194a and 194b in the pump housing. The door latches 192a, 192b engage with a slidable latch bar mechanism that is operatively connected to the slide clamp mechanism such that the slide clamp 115 can be inserted or ejected depending on a door open or a door closed position. For example, the latch bar mechanism may be spring biased towards the downstream side of the pump (e.g., to the left when looking at FIG. 1D) and as the door 120 is closed, the door latches 192a, 192b move the latch bar mechanism to the right as the door latches 192a, 192b are pressed into the pump housing.

The door 120 may also include a magnet 188 that is associated with a Hall effect sensor in the pump 100. The Hall effect sensor is configured to detect the presence of magnet 188 to determine whether the door 120 is closed.

In an example, as a user begins to move the door 120 from an open position (illustrated in FIGS. 1C and 1D) to a closed position (illustrated in FIGS. 1A and 1B), at least one of the valves 176a, 176b may occlude the tube 160 during the closing process.

Figure 2:
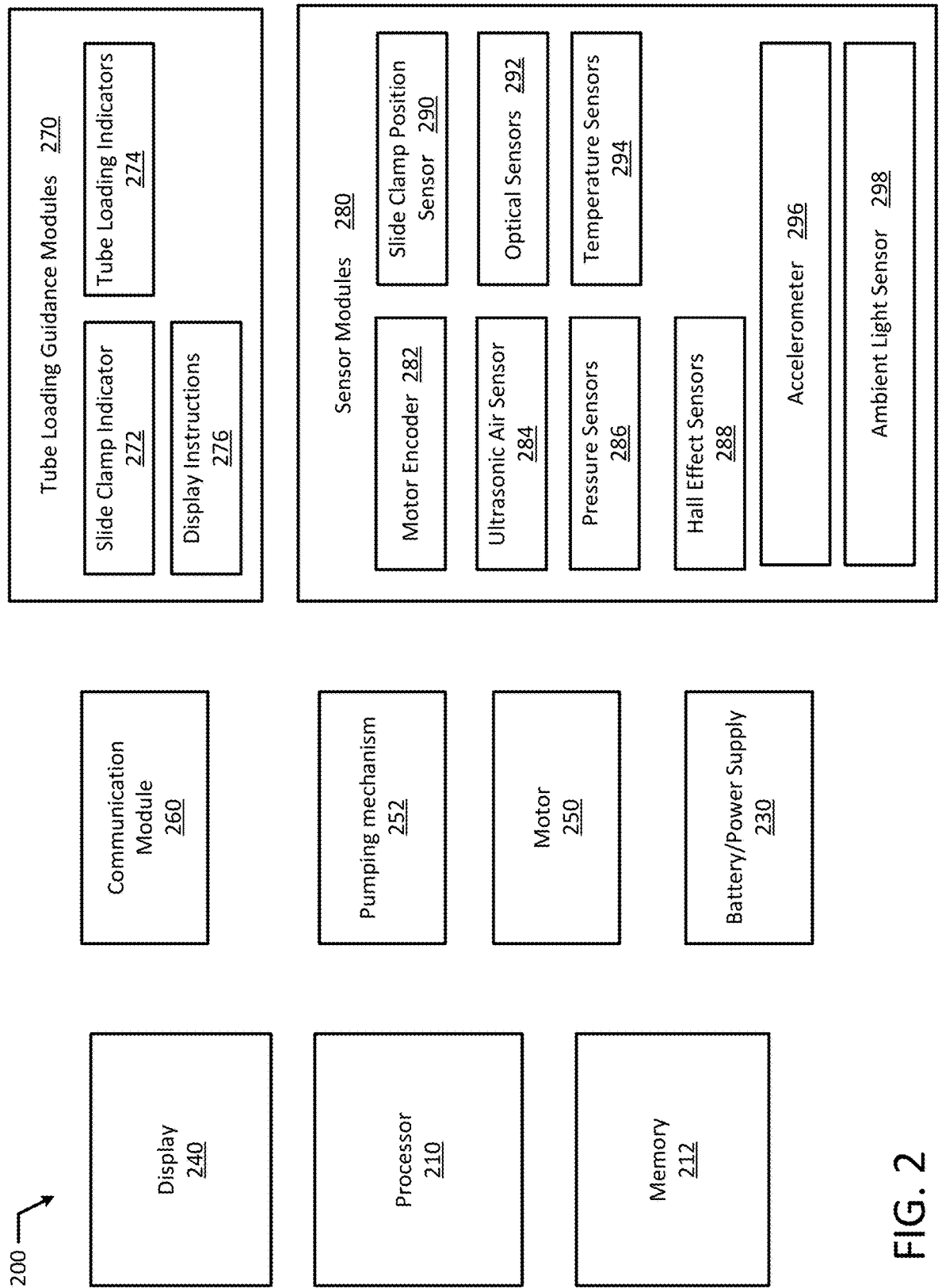
FIG. 2 illustrates a block diagram of an example infusion pump system according to an example embodiment of the present disclosure.
Figure 3A:
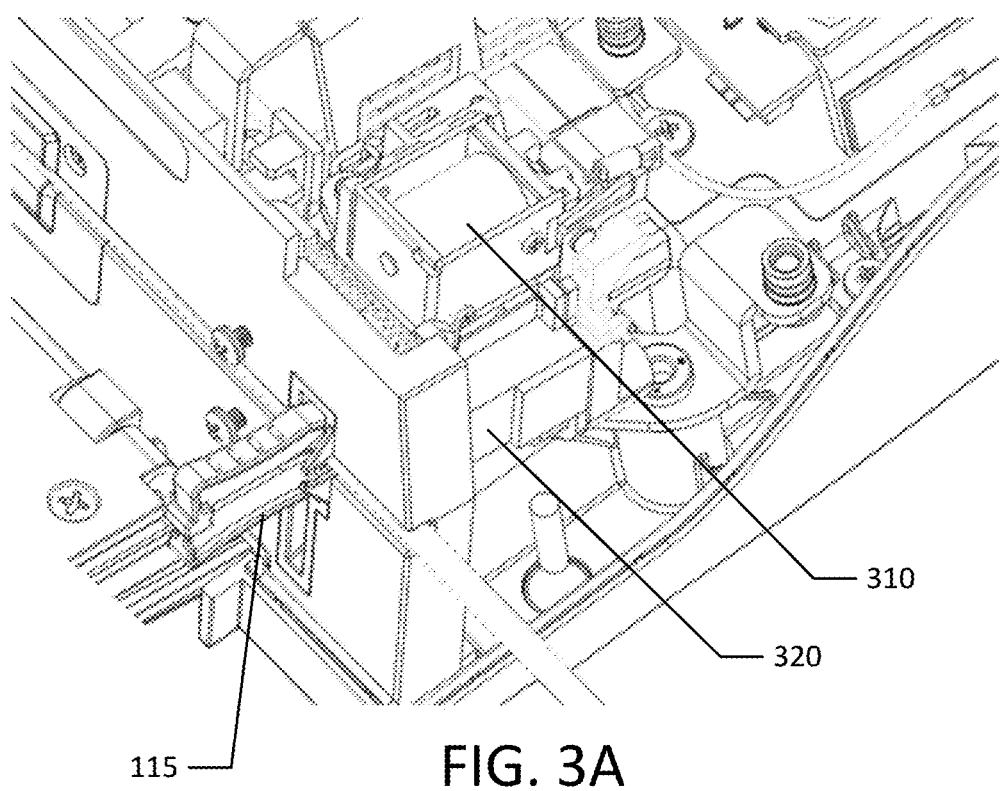
FIGS. 3A, 3B, 3C and 3D are isometric views of a solenoid actuated slide clamp ejection mechanism according to an example embodiment of the present disclosure.
Figure 3B:
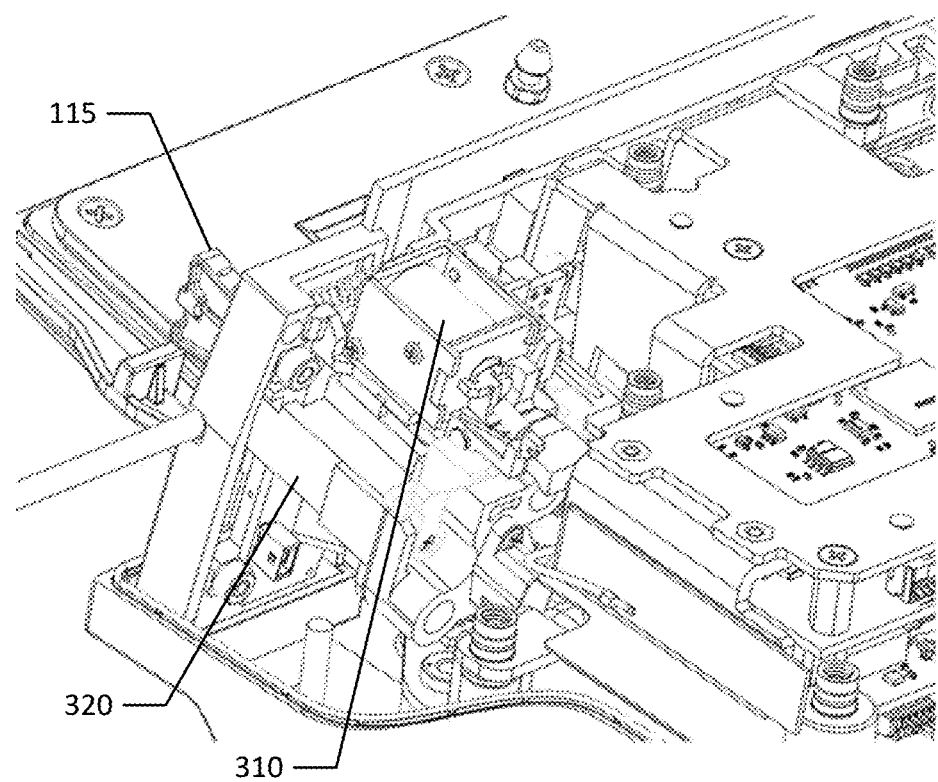
Figure 3C:
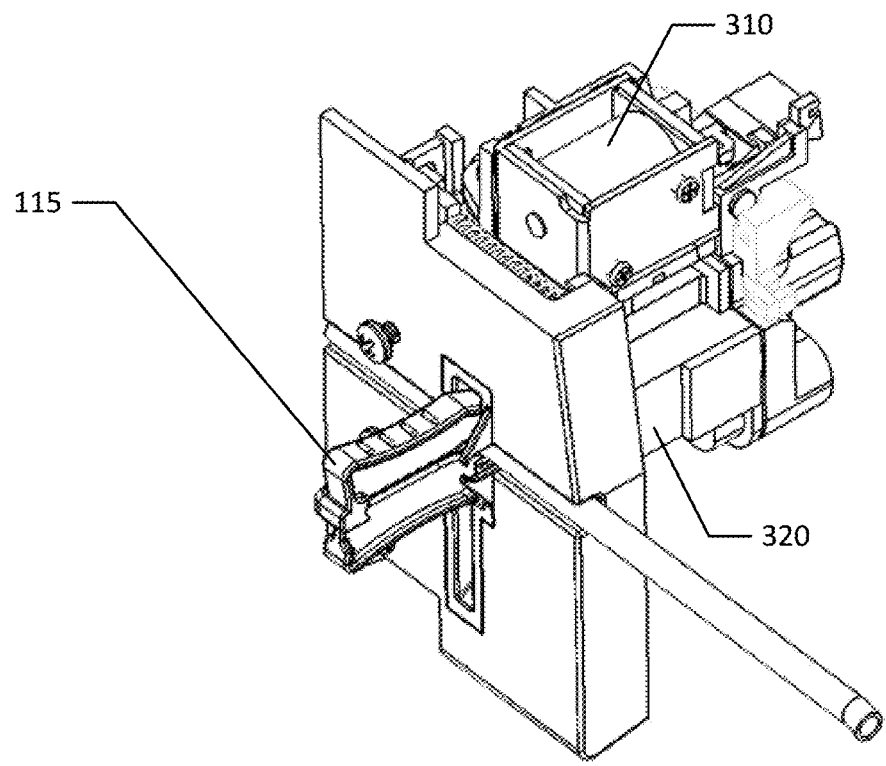
Figure 3D:
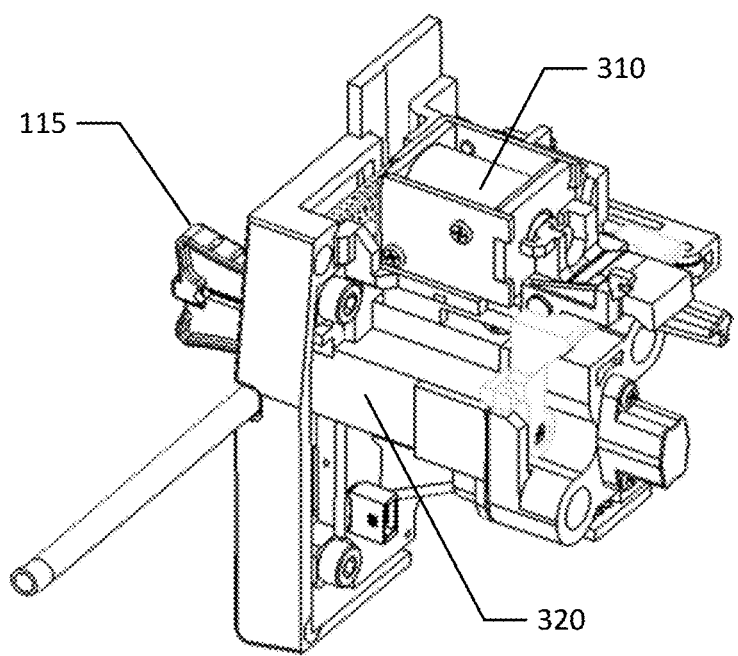

FIG. 2 depicts a high-level component diagram of an infusion pump system. The infusion pump system 200 includes a processor 210 in communication with memory 212, which is powered by a battery or power supply 230. The processor 210 communicates with a display 240, a motor 250 and associated pumping mechanism 252, and a communication module 260. The pump system 200 also may include tube loading guidance modules 270, such as a slide clamp indicator 272, tube loading indicators 274, and display instructions 276. Additionally, the infusion pump system 200 may include various sensor modules 280, such as a motor encoder 282, an ultrasonic air sensor 284, pressure sensors 286, Hall effect sensors 288, a slide clamp position sensor 290, optical sensors 292, temperature sensors 294, an accelerometer 296, and/or an ambient light sensor 298.

The power supply 230 may take many different forms. In one preferred embodiment, the power supply 230 may be in the form of a rechargeable battery unit. Additionally, the pump may be powered from an AC power supply. The AC power supply assembly has a power cord and an associated terminal that plugs into the housing. The AC power supply assembly has a plug that can be inserted into a standard electrical outlet to recharge the rechargeable battery when necessary. The AC power can also be supplied through the assembly to power the pump.

Sensors Associated with the Pump

The pump sub-assembly, as previously described, has associated therewith a plurality of sensors, which are operative to provide information as to the function and location of the various elements thereof. A drive motor shaft encoder comprises an encoder flag wheel attached to the armature shaft of the motor. The pump motor flag wheel may include a plurality of flags (e.g., twelve flags) extending radially outward from the hub thereof.

These flags act in concert with optical switches to fix the location of the armature shaft of the pump drive motor. The switches may further consist of a light emitting diode ("LED") and a photocell. An arrangement of two optical switches allows for a first switch to sense the edge of a flag, and the second switch to sense the middle of a subsequent flag. This arrangement allows for greater resolution of motor shaft position and direction as read by the encoder. For example, the resolution of the encoder may be approximately $\frac{1}{3072}$ of a rotation of the motor shaft.

The motor encoder senses shaft rotation directly. An index wheel may have a plurality of circumferentially coextensive radially disposed slots. Associated with these slots is an index wheel optical sensor. This sensor comprises a light emitting diode and an optical sensor or switch. In an example, the index wheel sensor is cooperative with the index wheel and the slots therein to provide positional information of the rotational location of the pump motor shaft.

In operation, the index wheel sensor acts in concert with the pump encoder to provide this positional information as well as directional information of the motor shaft. Associated with the shuttle itself is a linear gross position sensor. This sensor comprises a linear position Hall effect sensor and a plurality of magnets. Shuttle position sensor magnets present opposite poles to the shuttle Hall switch, so as to provide a field gradient operative to provide an indicium of the linear position of the shuttle.

The combination of the encoder and the other associated sensors aforementioned, provide inputs to a control mechanism, which may operate to accurately control the speed of the variable speed motor, the primary feature provided by such speed control is a temporal variability of the output of the pump. Additionally, such speed control allows for an electronically controlled linearization of the pump output per individual stroke as well as improving the time-integrated output of the pump.

The infusion pump may also include an ultrasonic air detection apparatus or transducer. The ultrasonic transducer acts in concert with a second transducer element to detect air within the IV tubing.

The pump allows the tube to be extended or stretched equally across the face of the associated sensor, thereby eliminating either a volumetric or stress gradient in the tube beneath the associated sensor so as to improve the accuracy of response of the sensor associated with, or connected to, housing. Essentially all of the sensors associated with, or actuated by, sensor arm execute the above described motion so as to achieve the above described result.

The pump may also include a downstream pressure sensor and a plurality of temperature sensors, which consist of thermistors.

The slide clamp may include a Hall effect sensor to identify the presence and/or position of the slide clamp 115.

Solenoid Actuated Slide Clamp

In an example, a solenoid actuated anti-free flow system may automatically eject the slide clamp 115. The automated ejection of the slide clamp 115 may utilize various sensors discussed herein to improve patient safety (e.g., avoid a free flow condition) and decrease errors of slide clamp ejection by confirming vital systems in the pump prior to ejection. The ejection of the slide clamp 115 may be automated after the system establishes that the IV tube is properly installed and loaded, the door is positively closed, and the respective sensors successfully perform system diagnostic checks.

In an example, a user may manually insert slide clamp 115 and then open door 120 of infusion pump 100 and the tube 160 may be positively held in an occluded state. After the door 120 is closed and proper loading is confirmed, the solenoid actuated anti-free flow system automatically ejects the slide clamp 115.

Various sensors within the infusion pump may be used for diagnostic checks. Hall effect sensors in the slide clamp 115 may be used to confirm that a slide clamp 115 is present. Pressure sensors (e.g., pressure sensors 174a, 174b) may confirm proper IV tube loading. Additionally, a Hall effect sensor (e.g., Hall effect sensor in housing 110 and associated magnet 188 in door 120) may confirm that the door 120 is closed. Optical sensors, such as optical IR sensors may confirm that the door is secured and latched. Additionally, pressure sensors may confirm that the door is closed and pressure is maintained. Hall effect sensors positioned within the latch may confirm that valve(s) are close. Any combination of the above sensors may be used for system diagnostic checks prior to slide clamp ejection. After the established set of sensors each successfully performs a system diagnostic check, a solenoid is energized and ejects the slide clamp 115.

Slide clamp ejection may also be governed by auxiliary monitoring systems that confirm other vital information such as patient information, medication information, clinician information, and pump information. Auxiliary devices connected to the patient may be used to confirm acceptability of a drug based on the patient's vital data.

Figure 4A:
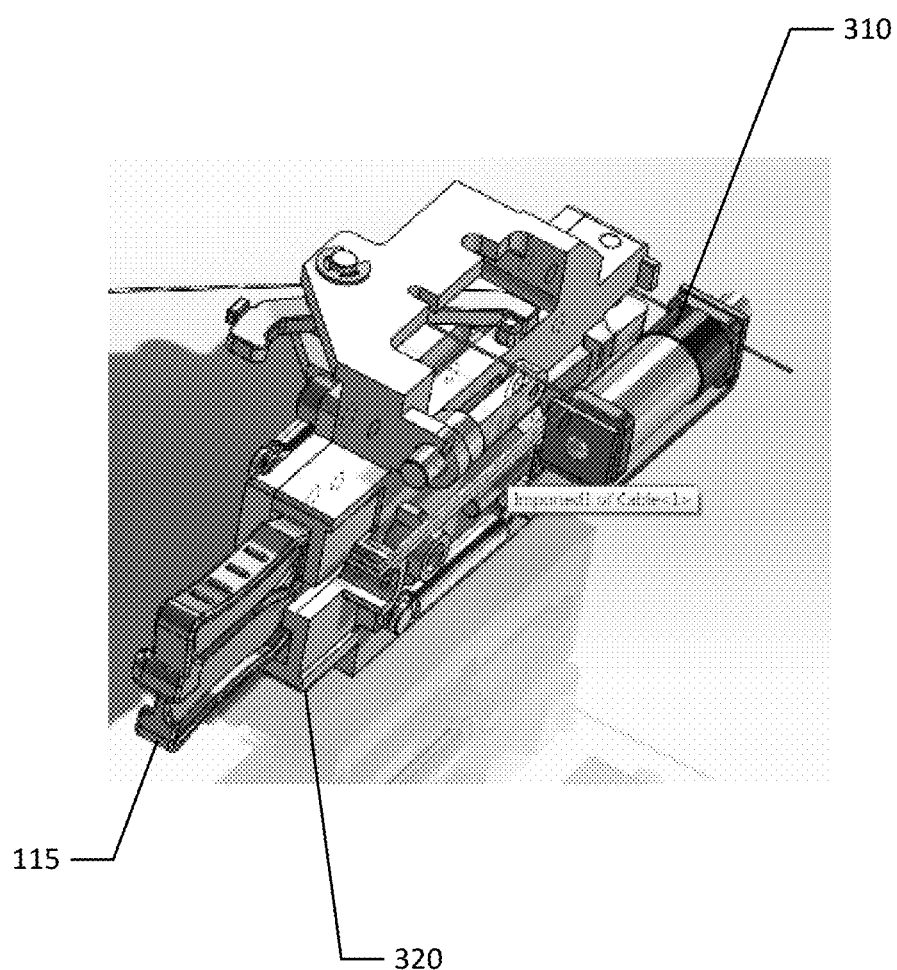
FIGS. 4A, 4B and 4C are alternative embodiments of automated slide clamp ejection mechanisms.
Figure 4B:
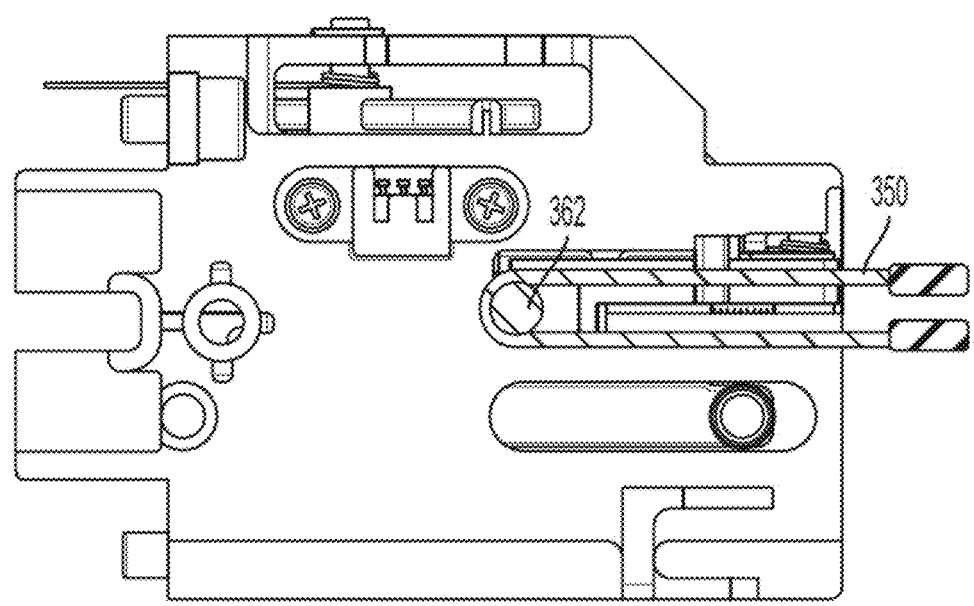
Figure 4C:
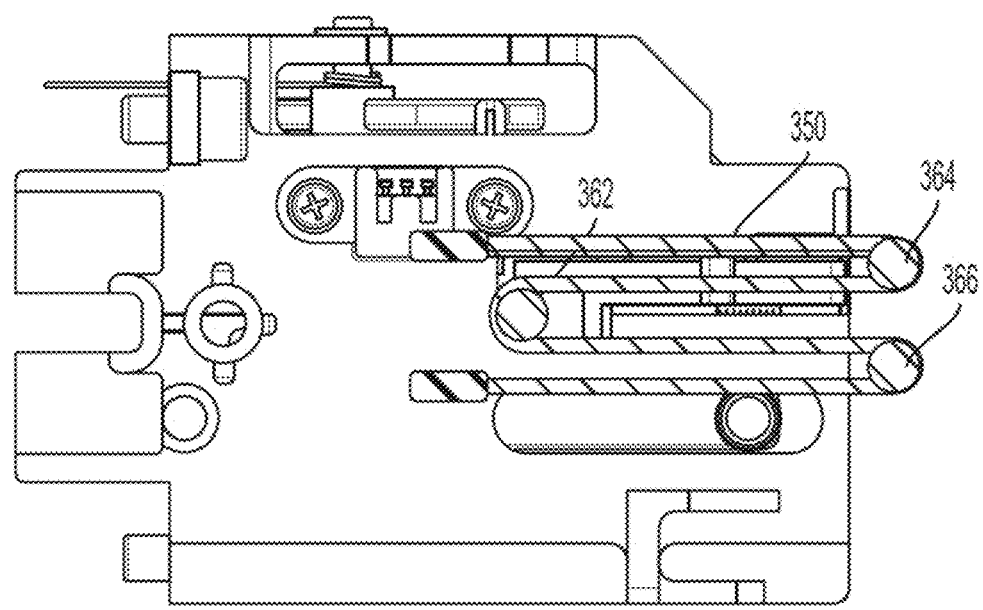

As illustrated in FIGS. 3A, 3B, 3C and 3D, the solenoid 310 is positioned within the pump housing 110 above the slide clamp channel 320. FIGS. 4A, 4B and 4C illustrate several alternative embodiments for auto slide clamp ejection. As illustrated in FIG. 4A, the solenoid 310 may also be positioned about the side of the slide clamp channel. Other mechanisms may be used for automated slide clamp ejection such as a motor or rack and pinion. A cam and follower mechanism may also be used. In another example, a shape memory wire 350 with an arrangement of pulleys 362, 364 and/or 366 may be activated for automated slide clamp ejection (as illustrated in FIGS. 4B and 4C). For example, the shape memory wire may have a first position (e.g., when the slide clamp is ejected) and a second position (e.g., when the slide clamp is loaded). When the slide clamp is ready to be auto ejected, an electrical current or heat may be applied to the wire so that the wire changes from the second position to the first position and automatically ejects the slide clamp 115.

Figure 5:
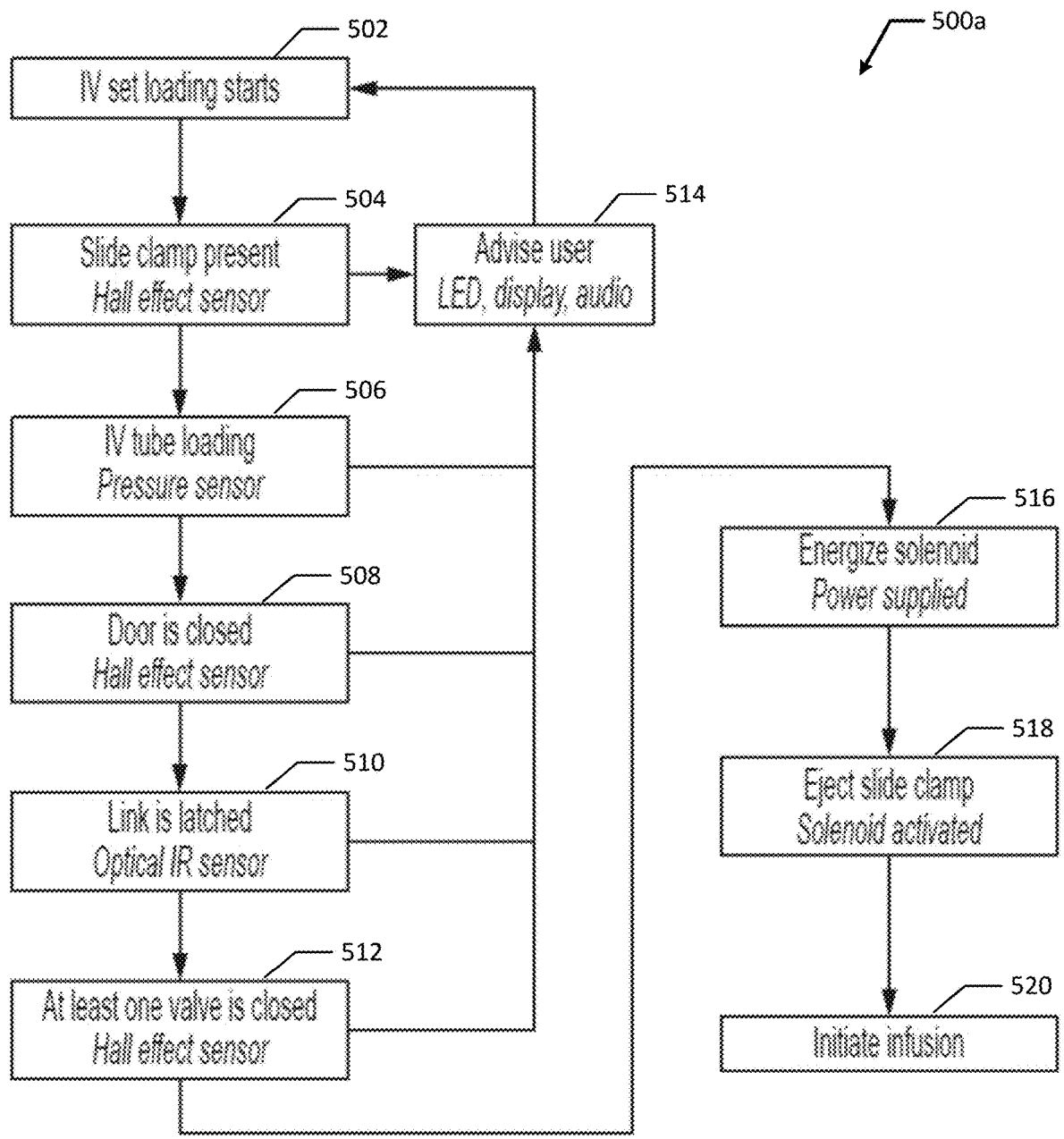
FIG. 5 is a flow chart of an example process for tube loading guidance according to an example embodiment of the present disclosure.

FIG. 5 illustrates an example IV set loading sequence 500a. For example, when IV tube loading starts (block 502), the Hall effect sensor in the slide clamp 115 detects that the slide clamp 115 is present (block 504). Then, the door 120 is opened and the IV tube 160 is loaded, which is confirmed by a pressure sensor (e.g., pressure sensors 174a, 174b) (block 506). Once the door 120 is closed, another Hall effect sensor (e.g., sensor associated with magnet 188) confirms that the door 120 is in the closed position (block 508) and an optical IR sensor confirms that the door link is latched (block 510). Then a Hall effect sensor confirms that at least one valve (e.g., valves 176a, 176b) is closed such that the IV tube 160 is closed (block 512). For each of blocks 504 to 512, the pump may provide tube loading guidance (LED, display, audio, etc.) as further described below (block 514). After each of the above sensors confirms that IV tube 160, door 120, and valve (e.g., valves 176a, 176b) are loaded and/or positioned, the pump 100 provides power to energize the solenoid (block 516). Then, the solenoid is activated to automatically eject the slide clamp 115 (block 518). Once the slide clamp 115 is ejected, the pump 100 may initiate an infusion (block 520).

Figure 6:
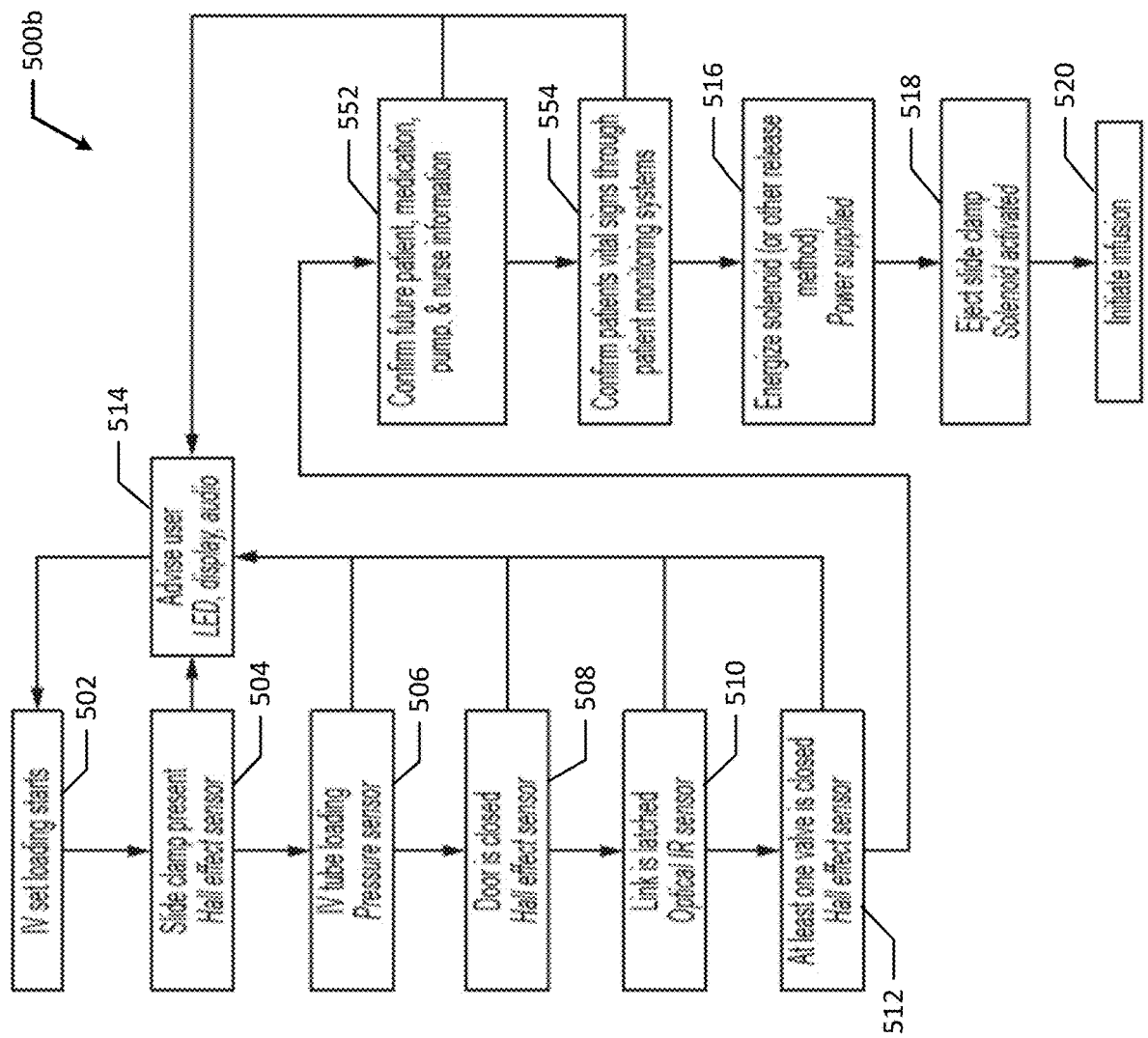
FIG. 6 is a flow chart of an example process for tube loading guidance according to an example embodiment of the present disclosure.

FIG. 6 illustrates an alternative IV set loading sequence 500b. For example, after the above sensors confirm loading and positioning of the pump components (e.g., blocks 502 to 512), the pump may also confirm patient, medication, clinician (e.g., doctor or nurse), and/or pump information (block 552). Patient's vital signs may also be confirmed through patient monitoring systems (block 554). Then, the solenoid may be energized and ejected (blocks 516 and 518) based on these additional safety checks and constraints.

Unlike systems that use mechanically timed slide clamp releases, the present disclosure provides additional patient safety that takes advantage of system diagnostic checks using a multitude of sensors to ensure proper tube loading and pump configuration.

Occlusion Detection

Occlusions may be detected by monitoring force and/or pressure measurements using various techniques. Additionally, the user may select between rapid occlusion detection and non-rapid occlusion detection. In rapid occlusion detection mode, the syringe pump 100 may report an occlusion at 50% of the force or pressure thresholds discussed below.

Difference Value from Baseline

A baseline force value (e.g., a moving or sliding average window of force measurement samples, such as twenty samples) may be taken after the motor starts. The force and/or pressure sensor may output an Analog to Digital Converter ("ADC") count. In an example, the baseline force value may be a window of 20 samples of ADC counts after the pump motor starts. The current force measurement may be monitored and a difference value (e.g., baseline force value subtracted from the current value) may be determined. If the difference value exceeds a predetermined threshold, an occlusion alarm may sound. The pump may have various settings for various occlusion detection sensitivities (e.g., Very High, High, Medium High, Medium, Low, and Very Low).

In an example, the syringe pump 100 may generate a high priority downstream occlusion alarm for the following fluid pressures and sensitivities: (Sensitivity—Very High; Occlusion pressure 50 psi; Lower Limit 25 psi; Upper Limit 52 psi); (Sensitivity—High; Occlusion pressure 16 psi; Lower Limit 13 psi; Upper Limit 18 psi); (Sensitivity—Medium High; Occlusion pressure 13 psi; Lower Limit 10 psi; Upper Limit 15 psi); (Sensitivity—Medium; Occlusion pressure 10 psi; Lower Limit 7 psi; Upper Limit 12 psi); (Sensitivity—Low; Occlusion pressure 7 psi; Lower Limit 4 psi; Upper Limit 9 psi); and (Sensitivity—Very Low; Occlusion pressure 4 psi; Lower Limit 1 psi; Upper Limit 6 psi).

In another example, the syringe pump 100 may generate a high priority downstream occlusion alarm for the following fluid pressures and sensitivities: (Sensitivity—Very High; Occlusion pressure 50 psi; Limit <52 psi); (Sensitivity—High; Occlusion pressure 16 psi; Lower Limit 12 psi; Upper Limit 20 psi); (Sensitivity—Medium High; Occlusion pressure 13 psi; Lower Limit 10 psi; Upper Limit 15 psi); (Sensitivity—Medium; Occlusion pressure 10 psi;

Lower Limit 7 psi; Upper Limit 12 psi); (Sensitivity—Low; Occlusion pressure 7 psi; Lower Limit 4 psi; Upper Limit 9 psi); and (Sensitivity—Very Low; Occlusion pressure 4 psi; Lower Limit 2 psi; Upper Limit 8 psi).

For an infusion pump, the tubing relaxes into the channel causing a change in force, which is dependent on temperature. For example, the tube material properties change based on temperature and a temperature compensation slope may be added for both the baseline force value as well as current ADC values. However, for a syringe pump, the syringe force contact is non-relaxing in nature and a change in temperature does not cause a material property change. Also, the force sensor for the syringe pump is rated and compensated to operate from −10 degrees to 40 degrees C., which covers typical pump operating ranges without affecting system level temperature variations in down stream occlusion ("DSO") detection for the syringe.

After the pump reaches steady state, occlusion detection may be based on a change in pressure or delta pressure instead of the High, Medium, or Low threshold settings. For example, after reaching steady state where the pressure is very steady, a sudden shift upwards for pressure may indicate that the pump is trending to occlusion. Monitoring a delta pressure after steady stay may allow for earlier occlusion detection.

In an example, steady state is achieved when there is less than a one (1) psi pressure change in the last two minutes of pressure measurements. If the system is not in a steady state condition, pressure delta sensing may be disabled.

The pump may also monitor changes in pressure as a function of flow rate. Different baseline and/or different threshold levels may be established based on the flow rate. For example, if the difference in pressure from baseline exceeds a predetermined relationship (e.g., pressure Increase=0.3*Flowrate in a 1 minute duration), an alert or warning for an occlusion sounds.

Slope of Pressure Measurements

An occlusion alarm may be generated if the slope calculated from the difference of two pressure measurements exceeds a threshold value. The pressure measurements may be taken in a predetermined window or time interval, for example, every two seconds. In an example, two different slope measurements may be used to account for any braking forces at the start of an infusion. To prevent false alarms, the initial threshold value may be higher to account for braking forces from the tubing or other pump components at start-up. After start-up, the threshold value may be lower after the pump has overcome the braking forces.

Area Under Force Curve

Occlusion detection may also be based on energy spent or the area between a base line and the current force line. The area calculation may be compared to a threshold value.

Downstream Tube Pull Detection

False alarms are an increasing issue in the infusion world. Patient movement may result in pulls or tugs of downstream tubing. This patient movement often leads to line management issues and it becomes increasingly challenging to differentiate between a false alarm from a true occlusion.

A pressure may be monitored where the pressure is equal to the current ADC minus baseline ADC multiplied by a factor of (1/DistCalSlope) (e.g., Pressure=(Current ADC−Baseline ADC)*1/DistCalSlope). The current ADC may be a window or continuous moving average of 50 samples of ADC counts taken during the pumping phase at 200 Hz. The baseline ADC may be a rolling sum of 50 samples of the first 50 ADC counts after the pump starts. The "DistCalSlope" term is a two-point slope (points taken at 2 psi and 15 psi) during manufacturing calibration. For example, the "DistCalSlope" term is equal to the difference of the ADC taken at 15 psi and 2 psi divided by the difference of the psi values (e.g., DistCalSlope=(ADC at 15 psi−ADC at 2 psi)/(15−2).

After the baseline ADC is determined, the baseline is held constant while the current ADCs are typically higher than the baseline ADCs. If the current ADCs are lower than the Baseline ADCs, then the baseline ADC may be updated to the current ADC. For example, the current ADC may be lower than baseline ADC due to tube relaxation and updating the baseline ADC to the current ADC accounts for the tube relaxation.

If the pressure calculated is greater than an established threshold, an occlusion is detected. Additionally, if an occlusion is detected, the pump may be stopped and a high priority occlusion alarm is communicated to the clinician.

As discussed above, the pump may have various settings for various occlusion detection sensitivities (e.g., Very High, High, Medium High, Medium, Low, and Very Low). Additionally, the lower limit may be updated to help distinguish tube-tugging and sudden drop scenarios from tube relaxation. In an example, if a tube pull or tug is detected, an alert or communication may be conveyed to the user to stop pulling on the tubing Accelerometer Digital moving average filters filter out unwanted spikes and/or noise signals. However, mechanically generated noise may also be unexpected and irregular which may lead to false alarms. In some instances, the mechanically generated noise may be more problematic than electrical noise.

An accelerometer may be used to help distinguish and/or filter mechanically induced sudden noises and/or spikes. Example sources of such noise may be from an operator pushing on the door of the infusion pump, an operator bumping into the pump, an operator moving the pump and patient while infusing, etc.

If the pump 100 drops from a height or an impact causes the pump to syphon or bolus, a separate high priority alarm can be sent to the user. If the accelerometer picks up mechanical movement/vibrations due to door movement or key selection (e.g., pressing display or physical keys), a feedback signal is sent to pump to not alarm or auto-restart because the event was purely caused by a sudden mechanically induced spike. Consequently, following an impact/drop a separate diagnostic algorithm is run on the sensors to test the functionality of the sensors and/or other critical components. For example, the diagnostic algorithm may ensure that the impact or drop did not disable or impair any of the sensor functions to ensure that the pump can detect and filter future vibration or drop events. When there is no impact but sudden irregular pressure spike(s) are detected by the occlusion algorithm, it can be confirmed from the accelerometer that it was purely electrically induced. If these spikes are sudden and irregular and not within an expected occlusion spike range an electrically induced sensor failure alarm is generated.

With an accelerometer sensitive enough to detect smaller movements/vibrations, a tubing tug or pulled scenario is confirmed in addition to the force sensor signal characteristics.

Figure 7:
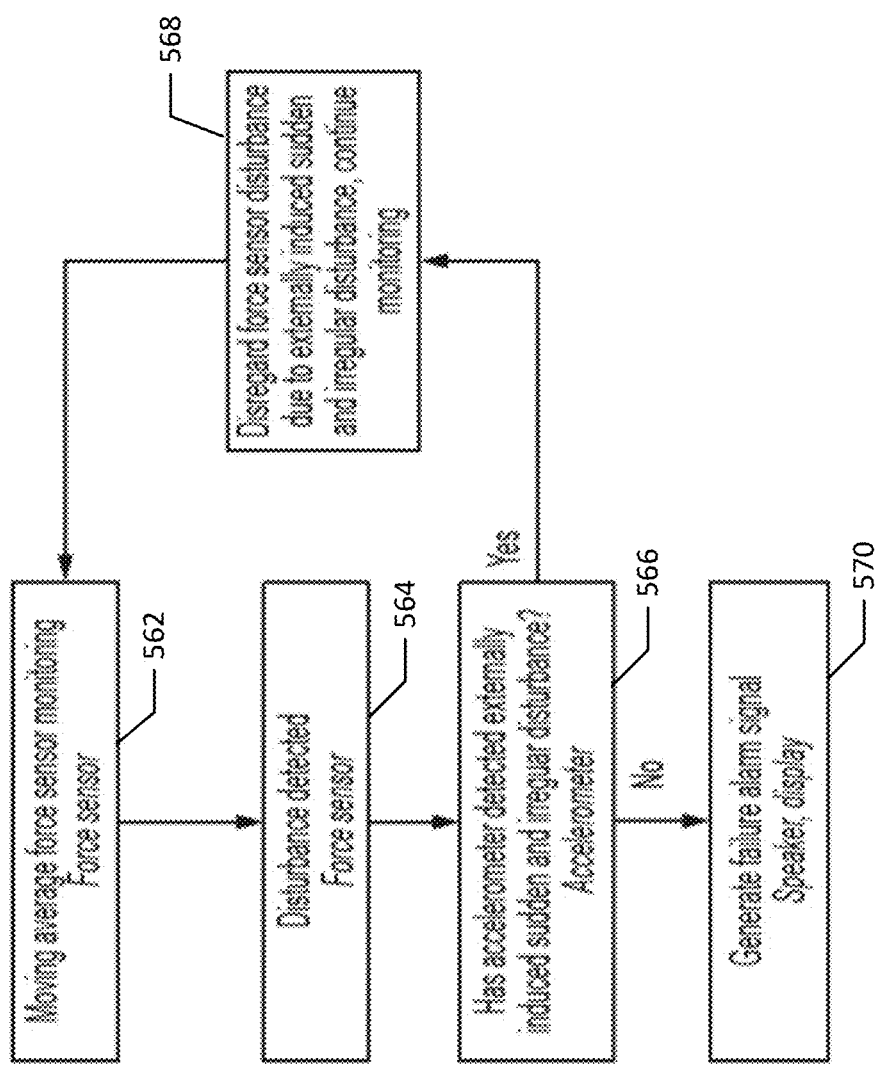
FIG. 7 is an example flow chart for detecting a disturbance of a pump using an accelerometer according to an example embodiment of the present disclosure.

As illustrated in FIG. 7, a moving average force sensor may monitor the forces applied to select locations on the pump (block 562). If a disturbance, or sudden pressure/force spike is detected (block 564), the system may check whether the accelerometer has detected an externally induced sudden or irregular disturbance (block 566). If the accelerometer has detected an externally induced and irregular disturbance, the pump may disregard the force sensor disturbance (block 568) and continue monitoring (block 562). However, if the accelerometer has not detected an external event, the pump may generate a failure alarm signal to indicate an alarm condition, such as the presence of an occlusion (block 570).

Tube Loading Guidance

Sensors within the infusion pump may also be used for tube loading guidance. The IV set or tube loading guidance advantageously provides clinical staff with visual confirmation of proper IV set or tube loading to ensure patient safety during infusion preparation. In an example embodiment, the display and visual cues may be positioned on the pump to provide visual guidance to user's during IV tube loading. The pump may be configured to detect a user's presence in the pump's proximity. For example, a Long Wavelength Infrared ("LWIR") system may detect a user's presence in the pump's proximity. In another example, an ambient light sensor may be used to detect a user's presence. As a user approaches the pump, the pump detects the user's presence and if there is no IV tube loaded, a visual cue is provided to indicate where to insert the slide clamp. For example, an illuminated ring or other shape may indicate where to insert the slide clamp. Simple point LEDs may also indicate where to insert the slide clamp.

Initially, the pump may be powered on without an IV tube loaded. At this stage, a light indicator for slide clamp loading may be pulsing or blinking. The rate of pulsing or blinking may depend on whether the pump is running off battery power or is plugged-in and is using a power cord. The display may be used to support a user with further visual guidance prior to the door opening. Then, the user may insert the slide clamp. After inserting the slide clamp, the slide clamp light changes color while the door opens and the light indicator around the perimeter of the slide clamp is now in an "ON" state indicating the next step to the user. As the user loads the IV tube throughout the IV tube channel, various critical loading points may include other visual and audio guidance to complete the IV tube loading sequence.

As illustrated in FIG. 8A, a rectangular shape 610a (e.g., slide clamp area) is illuminated, for example in a yellow color (e.g., yellow pulsing light), to indicate where the slide clamp 615 should be inserted (e.g., slide clamp slot 620). The color of illumination may also indicate that the slide clamp 615 has not yet been inserted (e.g., after insertion the yellow illumination may change to a green illumination). The display 630 may provide additional guidance to the user through instructions or prompts. For example, as illustrated in FIG. 8A, the display 630 may provide a message to the user, such as "To load the IV tube set, Insert slide clamp into opening."

After the user successfully loads the slide clamp 615, the illuminated shape 610 (e.g., rectangle around the slide clamp area) may change from a yellow color (as illustrated in 8A as rectangular shape 610a) to a green color (as illustrated in FIG. 8B as rectangular shape 610b) to indicate that the slide clamp 615 has been loaded. For example, the change from yellow to green may serve as a confirmation that this stage in the tube loading sequence has been properly completed. At this point, the user may open the door 640 and additional visual cues such as (e.g., LED lights 650 and 660) positioned behind the door, may guide the user for loading the tube.

Once the door is opened, the display 630 is no longer visible to the user, and colored LEDs 650, 660 are used to confirm various load points. In FIG. 8B, there are two different load points 670a, 670b that are indicated with LEDs 650, 660. Additionally LEDs or other visual cues may indicate other load points along the tube path.

The LEDs 650, 660 may originally display a first color (e.g., red or orange) if the tube has not been loaded or has been improperly loaded. The LEDs 650, 660 may then display a second color (e.g., green) once the tube has been properly loaded. In another example, the LEDs may pulse or blink to indicate whether a tube has been loaded. For example, a blinking LED may indicate that a tube is improperly loaded or unloaded and a solid colored LED may indicate that the tube is properly loaded at a respective load point. Initially, an indicator such as LED 650a may be pulsing orange to provide visual guidance and advise the user of the next tube-loading step. After the user loads the tube at a respective load point (e.g., load point 670a), the indicator (e.g., LED 650a) associated with that load point 670a may change from pulsing orange to a solid or steady green color. Then, the next indicator (e.g., LED 650b) associated with load point 670b may start pulsing to indicate the next loading step to the user.

Colors as well as animations may be used to indicate pump states and IV set or tube loading confirmations. For example, animations as well as pulsing, flashing or blinking lights may indicate the pump and IV tube loading states. It should be appreciated that any type of visual indicator or cue may be used and that LEDs are provided by way of example.

The pump may also use audible cues or tactile cues to inform or alert the user during tube loading. For example, the pump may use an assortment of beeps or vibrations to indicate the various stages of tube loading.

Figure 9A:
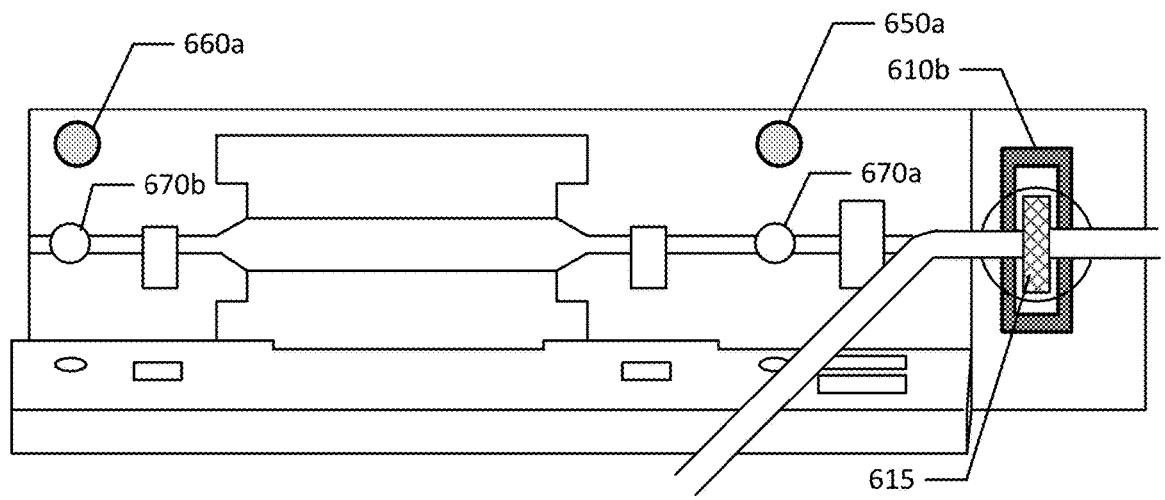
FIGS. 9A, 9B and 9C are partial views of an infusion pump with tube loading visual indicators, according to an example embodiment of the present invention.
Figure 9B:
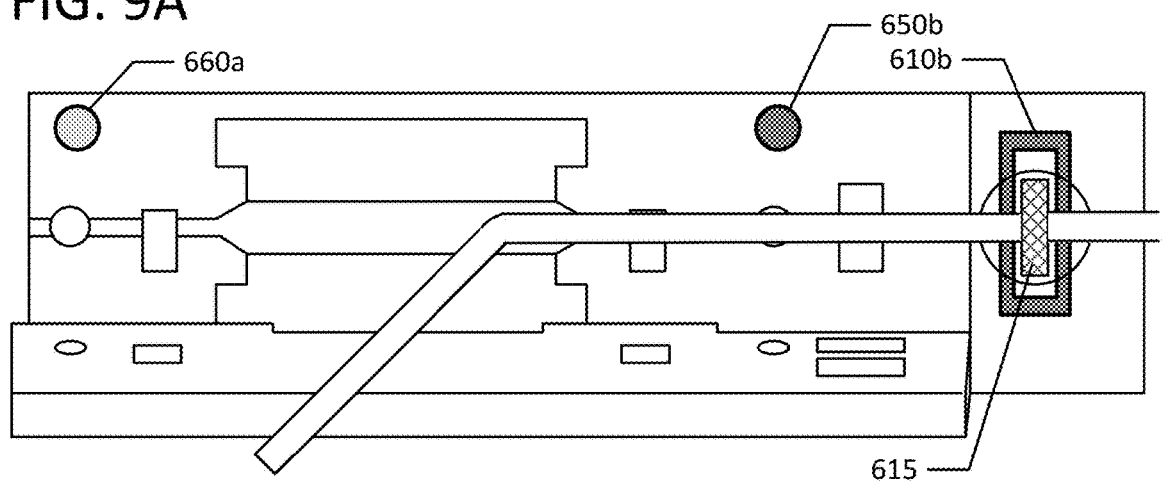
Figure 9C:
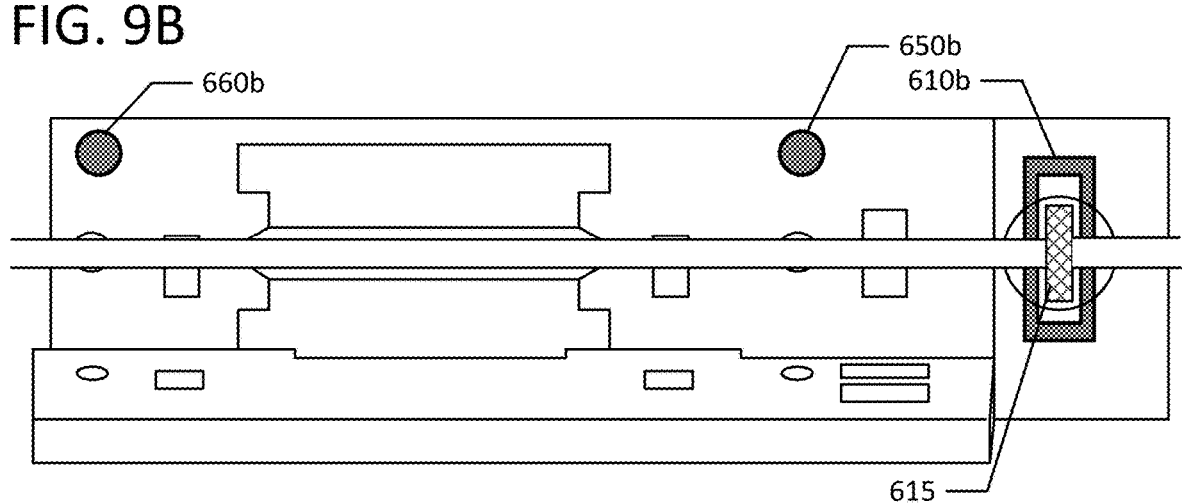

FIGS. 9A, 9B, and 9C illustrate example visual indicators during tube loading. In FIG. 9A, the slide clamp indicator area (e.g., rectangular shape 610b) is illuminated green after the slide clamp 615 has been successfully loaded. As the tube is loaded into each successive load point (e.g., load points 670a and 670b), the LED indicators 650 and 660 changes from red to green as illustrated in FIGS. 9B and 9C. The LED indicators may also change from yellow to green or any other color combination. As shown, the LEDs 650, 660 change from the first color to the second color once proper tube loading is detected and confirmed. Other visual indicators other than color may be used. Additionally, the indicators 650, 660 may have various geometries and shapes (e.g., circle, ring, triangle, square, etc.).

As illustrated in FIG. 9B, the tube is properly loaded in load point 670a and the LED indicator 650 changes from a first color (illustrated as 650a) to a second color (illustrated as 650b) to provide a visual cue to the user that the tube has been properly loaded. As discussed above, other cues may be provided to the user such as an audible beep. At this point in FIG. 9B, the tube has not yet been loaded into load point 670b, so LED indicator 660 is still in the first color (illustrated as 660a) to indicate that the tube has not been properly loaded at that load point.

As illustrated in FIG. 9C, the tube is properly loaded in load point 670b and the LED indicator 660 changes from a first color (illustrated as 660a) to a second color (illustrated as 660b) to provide a visual cue to the user that the tube has been properly loaded at that respective load point. After the tube has been properly loaded and the door is closed, the pump may be ready to program an infusion. Then, the slide clamp indicator area (e.g., rectangular shape 610b) may be activated in a different color to indicate to the user to eject the slide clamp and start the infusion.

As discussed herein, ejection of the slide clamp may occur automatically after confirmation from various sensors. However, in embodiments without automated ejection, after the user closes the door, a visual cue such as an illuminated area may indicate the location of the slide clamp ejection button. In another example, the button may be a backlight such that the entire slide clamp ejection button lights up for the user. Additionally, the display may prompt the user with a message, such as "Press button to eject slide clamp." Upon infusion completion, the slide clamp area may again be indicated by a light so that the door can again be opened by inserting the slide clamp.

In addition to color indication for slide clamp and tube loading guidance, LEDs may be cycled to indicate various stages of IV tube loading. For example, if a load has not yet been attempted, the LED may slowly pulse. If a load is completed successfully, the LEDs may be permanently on. Various LED colors may also be used to further distinguish the tube loading stages. Yellow may be used in a slow pulse or where the LED is slowly "breathing" to indicate that a load has not yet been attempted. Green may be used when the load is completed successfully, and the LEDs may be colored red when flashing to indicate that the load was not successful or that the IV popped out of a load point.

The guidance described herein advantageously improves patient safety by enhancing IV tube loading (e.g., insertion) guidance with confirmation of each completed loading step via visual and acoustic guidance. For example, tri-color or discrete color LEDS, light-guides, diffusers, light-guides with integrated diffusers, display screens, speakers and other acoustic elements (or a combination thereof) may be positioned on the pump and activated in specific combinations or sequences to provide guidance to the user while loading an IV tube.

Other Pump Guidance/Operational Indicators

Figure 10:
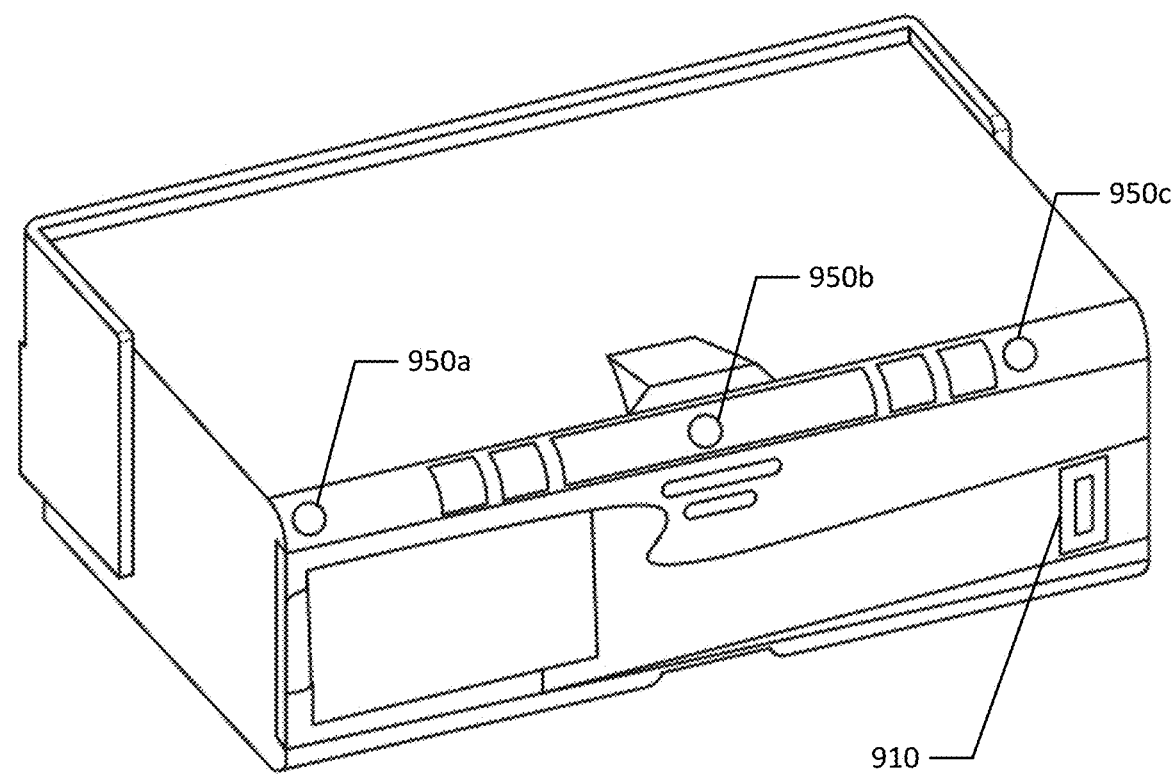
FIG. 10 is an isometric view of an infusion pump with visual indicators according to an example embodiment of the present invention.

The LEDs (e.g., 610, 650, 660 of FIGS. 8A to 9C or 910, 950*a-c* of FIG. 10) may also be used to indicate the pump is "ON" as well as flow direction. In some examples (e.g., with multi-colored LEDs such as tri-colored LEDs) the LEDs may be used to indicate some of the basic pump states when the display is off to reduce power consumption as illustrated in FIG. 10. As illustrated in FIG. 10, the load point LEDs (e.g., 950*a-c*) may be integrated on the external edge of the pump for improved visibility. Additionally, the LEDs 950*a-c* may be used to indicate pump status in a low power state consumption level.

The visual cues and/or other indicators such as audible cues and tactile cues may work in conjunction with the display to provide guidance and information to a user.

Operation of each of the above modes may be changed within the pump settings. Additionally, the display may depend on whether operation is from the power cord or battery. For example, to conserve the battery, the LED (e.g., 610, 650, 660 of FIGS. 8A to 9C or 910, 950*a-c* of FIG. 10) and other light indicators may be used. However, when operating via a power cord, both the LED/light indicators and the display may be used to provide visual indications and prompts to the user.

Rack Power Management

The infusion pump disclosed herein and/or a syringe pump may be used with a rack configured to house one or more pumps (e.g., infusion and/or syringe pumps). The rack may provide dynamic power and heat management for each pump housing within the rack. The power and heat management may be based on medication criticality that each respective pump is delivering. For example, a pump housed in the rack that is delivering a highly critical medication may be allocated more power so that the battery is charged to a level that reduces risk to the patient from a depleted battery after AC has been removed.

The rack may assist with pump identification, pump-to-pump communication, pump-to-rack and rack-to-pump communication, pump battery charging, etc. The rack may also manage power based on medication criticality and may also manage motor consumption per medication needs.

The rack may provide a common display and external connectivity via a wired or wireless connection.

The rack may implement several methods or procedures to control battery consumption and charging of the various infusion pumps and/or syringe pumps housed in the rack. The rack may allow a pump power supply or wall wart to draw higher current for faster charging. For example, the rack may allocate rack power to each pump such that its battery will be charged to a level that reduces risk to a patient from a depleted battery after AC-power has been removed. If a patient is receiving a critical medication along with a noncritical IV solution, the pump delivering the critical therapy may be given charging priority such that it is allowed to charge its battery faster than other pumps housed in the rack. The rack may also manage the amount of power that a pump is using for things other than battery charging, such as driving its motor. If one pump is using more power to drive its motor then that pump may be allowed to have a higher charge current so that when unplugged, the run time on the battery will be similar for all pumps housed in the rack. The rack may also prioritize and assign fast charging vs. trickle charging on a pump-to-pump basis based on criteria, such as charge need, medication being delivered, etc.

The rack may also detect failure modes, such as exceeding thermal constraints on power supplies.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention claimed is:

1. An infusion pump comprising:
    a housing with a door pivotally mounted to the housing;
    a tube channel positioned at least partially behind the door on the housing, the tube channel configured to hold a tube in the infusion pump;
    a pumping mechanism; and
    a slide clamp ejection device including a solenoid in operable contact with a slide clamp thereby configured to automatically eject the slide clamp from a channel based on one or more inputs from one or more pressure sensors configured to detect the presence of the tube at a load point along the tube channel and one or more additional sensors arranged on the infusion pump, wherein the slide clamp is automatically ejected from the channel when the one or more inputs establish that the tube is installed and loaded, and the door is in a closed state where the door is closed and latched.

2. The infusion pump of claim 1, wherein the door is configured to unlock and transition between a closed state and an open state after the slide clamp is inserted within the channel.

3. The infusion pump of claim 1, further comprising an accelerometer, wherein the accelerometer is configured to detect at least one of an occlusion or whether the infusion pump experienced an external impact.

4. The infusion pump of claim 1, wherein the infusion pump is positioned in a rack with at least one other infusion pump or syringe pump.

5. The infusion pump of claim 1, further including a sensor, wherein the sensor detects the presence of the slide clamp within the channel.

6. The infusion pump of claim 5, wherein the sensor is a Hall effect sensor.

7. The infusion pump of claim 1, further comprising a tube loading guidance system, wherein the tube loading guidance system includes one or more visual cues configured to provide guidance to a user during tube loading.

8. The infusion pump of claim 7, wherein the visual cues include a first light-emitting diode, a second light emitting diode, and a display, wherein the first and second light emitting diodes are configured to indicate whether a tube is properly or improperly loaded at respective load points on the infusion pump.

9. The infusion pump of claim 1, further comprising an occlusion sensor, wherein the occlusion sensor is configured to determine if an infusion line connected to the infusion pump is blocked.

10. The infusion pump of claim 9, wherein the occlusion sensor determines if an infusion line is blocked by calculating one of a slope of a force curve, a slope of a pressure curve, a comparison to a baseline force measurement, a comparison to a baseline pressure measurement, or an area under the force curve.

11. The infusion pump of claim 1, wherein the tube is in an occluded state after the slide clamp is inserted within the channel.

12. The infusion pump of claim 11, wherein the one or more additional sensors include at least one of a first Hall effect sensor configured to detect when the door is positioned in a closed state, an optical IR sensor configured to detect when the door is latched while positioned in the closed state, and a second Hall effect sensor configured to detect that a valve is closed to place the tube in an occluded state.

13. The infusion pump of claim 12, wherein the infusion pump is configured to initiate an infusion after receiving a confirmation that the slide clamp is in an ejected state and the door is in the closed state.

* * * * *